US006365394B1

(12) United States Patent
Gao et al.

(10) Patent No.: US 6,365,394 B1
(45) Date of Patent: Apr. 2, 2002

(54) CELL LINES AND CONSTRUCTS USEFUL IN PRODUCTION OF E1-DELETED ADENOVIRUSES IN ABSENCE OF REPLICATION COMPETENT ADENOVIRUS

(75) Inventors: Guangping Gao, Rosemont; James M. Wilson, Gladwyne, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/659,203

(22) Filed: Sep. 11, 2000

Related U.S. Application Data
(60) Provisional application No. 60/156,644, filed on Sep. 29, 1999.

(51) Int. Cl.⁷ .......................... C12N 7/00; C12N 15/64; C12N 7/02; C12P 1/00
(52) U.S. Cl. ...................... 435/239; 435/367; 435/455; 435/456; 435/464; 435/465; 435/476; 435/235.1; 435/70.3
(58) Field of Search ........................ 435/41, 69.1, 70.3, 435/91.21, 91.42, 456, 173.3, 235.1, 236, 239, 367, 455, 476, 325, 465, 464

(56) References Cited

U.S. PATENT DOCUMENTS
5,891,690 A    4/1999   Massie .................... 435/172.3

FOREIGN PATENT DOCUMENTS
WO    WO 97/00326    1/1997

OTHER PUBLICATIONS

Guang–Ping Gao et al, "A Cell Line for High–Yield Production of E1–Deleted Adenovirus Vectors without the Emergence of Replication–Competent Virus", Human Gene Therapy, 11:213–219 (Jan. 1, 2000).

Imler et al. 1996. Novel complementation cell lines derived from human lung carcinoma A549 cells support the growth of E1–deleted adenovirus vectors. Gene Therapy. vol. 3: 75–84.*

Dai, Y. et al., "Cellular and Humoral Immune Responses to Adenoviral Vectors Containing Factor IX Gene: Tolerization of Factor IX and Vector Antigens Allows for Long Term Expression." Proc. Natl. Sci., U.S.A., 92: 1401–1405 (Feb. 1995).

Fallaux, F.J. et al., "New Helper Cells and Matched Early Region 1–Deleted Adenovirus Vectors Prevent Generation of Replication–Competent Adenoviuruses." Hum. Gene Ther., 9: 1909–1917 (Sep. 1, 1998).

Gao, G.P., et al., "Biology of Adenovirus Vectors with E1 and E4 Deletions for Liver Directed Gene Therapy." J. Virol., 70: 8934–8943 (Dec. 1996).

Gilgenkrantz, H., et al., "Transient Expression of Genes Transferred In Vivo into Heart Using First–Generation Adenoviral Vectors: Role of the Immune Response." Hum. Gene Ther., 6: 1265–1274 (Dec. 1995).

Habib, N.A.., et al., "A Phase I/II Study of Hepatic Artery Infusion with stp53–CMV–Ad in Metastatic Malignant Liver Tumors."Hum. Gene Ther., 10:2019–2034 (Oct. 1999).

Hehir, K.M., et al., "Molecular Characterization of Replication–Competent Variants of Adenovirus Vectors and Genome Modification to Prevent their Occurrence." J. Virol., 70:8459–8467 (Dec. 1996).

Imler, J.–L., et al., "Trans–Complementation of E1–Deleted Adenovirus: A New Vector to Reduce the Possibility of Co–Dissemination of Wild Type and Recombinant Adenoviruses." Gene Ther., 3:75–84 (Jun. 1995).

Imler, J.–L., et al., "Novel Complementation Cell Lines Derived From Human Lung Carcinoma A549 Cells Support the Growth of E1–Deleted Adenovirus Vectors." Gene Ther., 3: 75–84 (Jan. 1996).

Lochmuller, H., et al., "Emergence of Early Region 1–Containing Replication–Competent Adenovirus in Stocks of Replication–Defective Adenovirus Recombinants (ΔE1 and ΔE3) During Multiple Passages in 293 Cells." Hum. Gene Ther., 5: 1485–1491 (Dec. 1994).

Wilson, J.M., et al., "Gene Therapy of Cystic Fibrosis Lung Disease Using E1 Deleted Adenoviruses: A Phase I Trial." Hum. Gene Ther., 5: 501–519 (Apr. 1994).

Yang, Y., et al., "Cellular Immunity to Viral Agents Limits E1–Deleted Adenoviruses for Gene Therapy." Proc. Natl. Acad. Sci., U.S.A. 91: 4407–4411 (May 1994).

Zhou, H., et al., "Development of a Complementing Cell Line and A System for Contruction of Adenovirus Vectors with E1 and E2a Deleted." J. Virol., 70:7030–7038 (Oct. 1996).

Zhu. J.D., et al., "Characterization of Replication–Competent Adenovirus Isolates from Large Scale Production of a Recombinant Adenoviral Vector." Hum. Gene Ther., 10: 113–121 (Jan. 1, 1999).

* cited by examiner

Primary Examiner—Laurie Scheiner
Assistant Examiner—Shanon A. Foley
(74) Attorney, Agent, or Firm—Howson and Howson

(57) ABSTRACT

Novel cell lines useful for trans-complementing E1-deleted adenoviral vectors are described. The cell lines are capable of providing high yields of E1-deleted adenoviral vectors in the absence of replication-competent adenovirus over multiple passages.

22 Claims, 2 Drawing Sheets

CELL LINES AND CONSTRUCTS USEFUL IN PRODUCTION OF E1-DELETED ADENOVIRUSES IN ABSENCE OF REPLICATION COMPETENT ADENOVIRUS

CROSS-REFERENCE TO RELATED APPLICATION

This application claims the benefit of the priority of U.S. patent application Ser. No. 60/156,644, filed Sep. 29, 1999 now abandoned.

This work was supported by NIDDK (DK47757-06 & DK49136-05), NHLBI (HL49040-08) and NICHD (HD32649-05) of the National Institutes of Health. The U.S. government may have certain rights in this invention.

FIELD OF THE INVENTION

This invention relates generally to the field of constructs and methods for producing viral vectors, and more particularly, for the production of adenoviruses.

BACKGROUND OF THE INVENTION

Recombinant adenoviruses have been described as useful for delivery of transgenes to cells for a variety of purposes, including both therapeutic and prophylactic (vaccine) uses. However, successful commercialization of E1-deleted adenoviruses will require suitable manufacturing processes, which have yet to be developed. Infection of an E1 trans-complementing cell line with the vector and purification of the resulting lysate is a simple and scalable process that yields sufficient quantities of product. Unfortunately, production of E1-deleted adenovirus vectors for gene therapy has been plagued by emergence of replication competent adenovirus (RCA) caused by homologous recombination between the vector and transfected E1 gene.

Several strategies have been described to avoid RCA. However, to date none of these approaches has resulted in an E1-complementing cell line which is stable and produces high yields of E1-defective adenoviruses in the absence of detectable RCA.

J. -L. Imler et al., *Gene Ther.*, 3:75–84 (1996) describes an A549 cell stably transfected with E1a and E1b open reading frames (ORFs) and contiguous pIX gene. The E1a was driven by phosphoglycerate kinase promoter and RCA was reportedly eliminated. However, more recent publications describing this system reveal that Imler was unable to detect E1b protein expression. See, Introgene, WO 97/00326, published Jan. 3, 1997.

This Introgene application described an alternative system to that of Imler, cited above. This application describes cell lines derived from certain human diploid cells with E1a and E1b expressed, but no pIX (ECACC NO. 96022940). The cells were produced by transfection of human embryonic retinoblast (HER) cells with a vector containing nt 459–3510 of Ad, which corresponds to E1a, E1b, but excludes the E1a promoter, a portion of the E1b gene encoding the E1b 8.3 kb protein, and any pIX sequences.

Another system for avoiding RCA is described in Massie, U.S. Pat No. 5,891,690. The patent describes an Ad E1-complementing cell line having a stably integrated complementation element comprising a portion of the Ad E1 region covering the E1a gene and the E1b gene, but lacking the 5' ITR, the packaging sequence, and the E1a promoter. Further, the E1a gene is under control of a first promoter element and the E2b gene is under control of a second promoter. A specific cell line described and claimed by Massie contains nt 532–3525 of Ad5, which includes E1a, the E1b promoter, and a portion of the E1b gene. This cell line does not contain the carboxy terminus of the E1b gene, which encodes the 8.3 kb product, nor does it contain pIX gene sequences.

What is needed in the art is a stable E1-complementing cell line, which expresses all adenoviral E1a and E1b gene products, and which produces high yields of E1-defective adenoviruses in the absence of detectable RCA.

SUMMARY OF THE INVENTION

Advantageously, the present invention provides E1 expressing cell lines that are stable, can be adapted to suspension culture in serum free medium, and yields high quantity of vector. Significantly, the cell lines allow isolation and subculture of E1-deleted recombinant adenoviruses in an environment free of replication competent adenovirus (RCA). Further, the cell lines of the invention effectively plaque vector to allow isolation and subculture of new recombinants in an environment free of RCA.

Thus, in one aspect, the invention provides an E1-complementing cell line useful for production of recombinant E1-defective adenoviruses in the absence of detectable replication-competent adenovirus. The E1-complementing cell line contains an aneuploid cell line stably transformed with a nucleic acid molecule comprising nucleic acid sequences encoding adenovirus E1a and adenovirus E1b under the control of a phosphoglycerate kinase (PGK) promoter. Suitably, the nucleic acid molecule lacks adenovirus sequences 5' to the sequences encoding adenovirus E1a.

In another aspect, the invention provides a method for packaging of E1-defective adenoviral particles in the absence of replication competent adenovirus. The method involves introducing a vector into cells from the E1-complementing cell line of the invention, where the vector contains a defect in the adenovirus E1 region, adenovirus 5' and 3' cis-elements necessary for replication and packaging, adenovirus pIX, and regulatory sequences necessary for expression of the adenoviral genes and transgene.

In another aspect, the invention provides a method of producing E1-defective adenoviral particles in the absence of detectable replication competent adenovirus. The method involves infecting cells from the E1-complementing cell line of the invention with an E1-defective adenovirus and culturing under conditions which permit the cell to express the E1a and E1b proteins.

Other aspects and advantages of the invention will be readily apparent from the following detailed description of the invention.

DETAILED DESCRIPTION OF THE INVENTION

Figure 1:
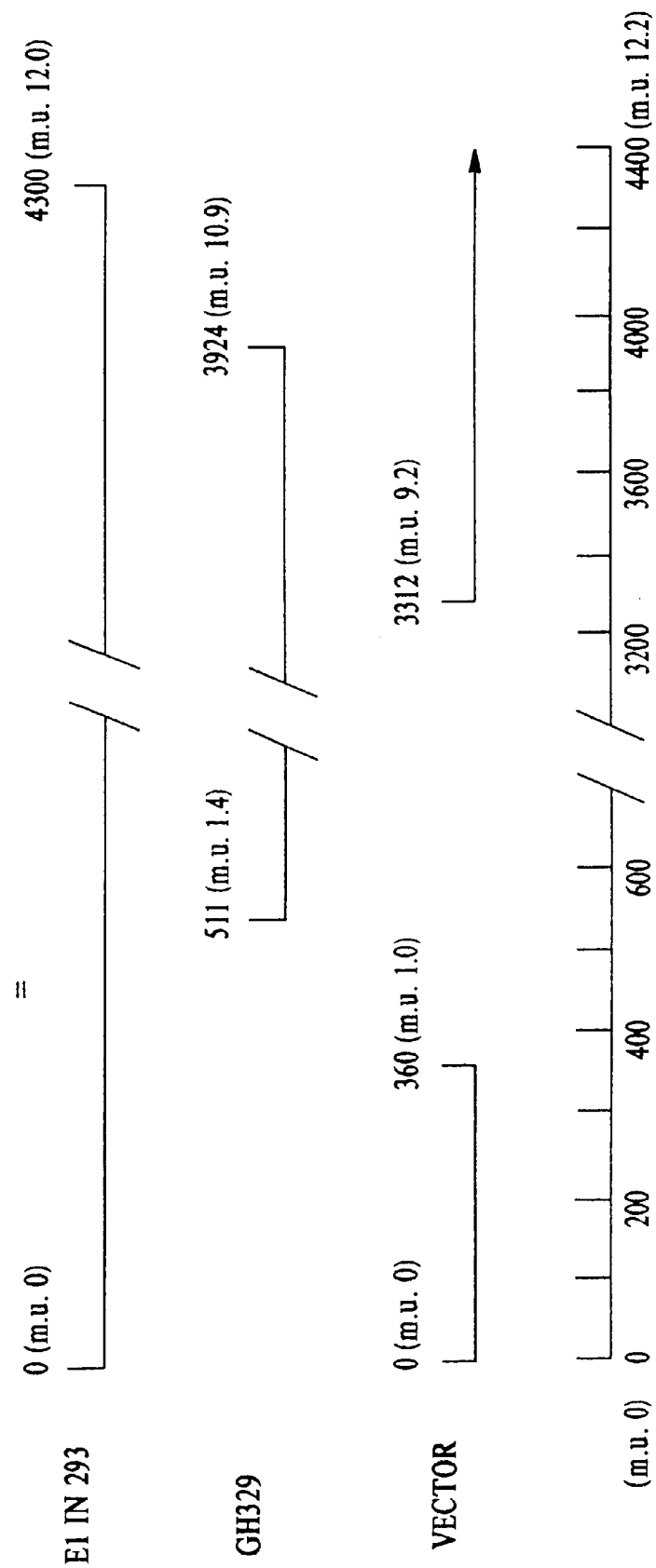
FIG. 1 is a schematic representation of the structures of the E1-deleted recombinant adenoviral vector, Ad5 DNA sequence in 293 cells and PGK Ad5E1 fragment in the new E1 cell line.

The present invention provides a method of producing E1-deleted adenoviruses in the absence of detectable replication-competent adenovirus (RCA), as well as cell lines and vectors useful in this method. The resulting E1-deleted adenoviruses are particularly well suited for use in delivering genes to a mammal, because these adenoviruses are substantially free of contaminating RCA.

In one desirable embodiment, the invention provides HeLa based cell lines that stably expresses the E1 locus from a promoter derived from the phosphoglycerate kinase (PGK) gene. These cell lines have no adenoviral sequences 5' to the E1 open reading frame (ORF) and reduced (or no) homology 3' to E1. These cell line supports plaquing and amplification of E1-deleted vectors at levels equal to or better than 293 cells without the emergence of RCA.

One example of such a cell line is the GH329 cell line, which has been deposited with the American Type Culture Collection (ATCC), 10801 University Boulevard, Manassas, Va. 20110–2209, USA on Sep. 29, 1999, and has been assigned accession number PTA-803. This deposit has been made pursuant to the provisions of the Budapest Treaty and in conformity with the requirements of 37 CFR §§1.801 et seq. The GH329 cells been found to complement (and allow the replication of) E1-deleted viral vectors in the absence of detectable replication competent adenoviruses (RCA) over at least 20 passages. Currently, GH329 is believed to express a single copy of each the E1a and E1b proteins. However, yields obtained using the GH329 cell line are at least equivalent to those obtained in 293 cells, in which RCA is observed following 5 to 10 passages.

Another suitable cell line is the GH364 cell line, which expresses between 5 to 10 copies of the E1a and E1b proteins. The GH364 cell line was deposited with the ATCC on May 24, 2001 and has been assigned accession number PTA-3405. Yet another cell line of the invention is the GH354 cell line. The GH354 cells have been found to complement (and allow replication of) E1-deleted viral vectors in the absence of detectable RCA over at least 20 passages. Further, as with the GH329 cell line, yields obtained using the GH354 cell line are at least equivalent to those obtained in 293 cells. The GH354 cell line was deposited with the ATCC on May 24, 2001 and has been assigned accession number PTA-3404. The deposits for both the GH364 and GH354 cell lines were made pursuant to the provisions of the Budapest Treaty and in conformity with the requirements of 37 CFR §§1.801 et seq.

The cell lines of the invention are particularly well suited for production of E1-deleted adenovirus for preclinical and clinical use, as they are readily adapted to growth in serum free media. The cell lines of the invention, e.g., GH329, may be adapted to growth in serum-free media using techniques well known those of skill in the art. These serum-free-media adapted cell lines are encompassed by the present invention.

Optionally, other useful cell lines may be derived from a cell line of the invention. For example, the GH329 (or GH354 or GH364) cell line may be modified to stably express another desired protein(s) using the techniques described herein, as well as techniques known in the art. In one desirable embodiment, a derivative of the GH329 cell line may be produced by stably transforming GH329 cells such that they contain one or more sequences expressing adenoviral proteins (or functional fragments thereof) required for replication of the E1-deleted virus. In addition to the adenoviral E1a and E1b functions provided by the cell line, the required adenoviral functions include E2a and E4 ORF6. Thus, in one embodiment, a GH329 derivative cell line may be produced which expresses the required functions of the E2 region or E4 region, or combinations thereof Suitably, the nucleic acid molecule(s) used to produce the GH329 derivative cell line contains no adenoviral sequences 5' to the E1 coding region and only the minimal adenoviral sequences required to express the desired functional proteins in the host cell. Given this information) one of skill in the art may readily engineer other GH329 derivative cell lines.

I. E1-Complementing Cell Line
A. Target Cells

The vector used to transform HeLa cells and produce the GH329 cell line of the invention may be used to develop other E1-trans-complementing cell lines. Preferably, such other cell lines are derived from HeLa cells, an aneuploid epithelial-like cell derived from cervical carcinoma [ATCC CCL2]. However, using the vector described herein, another mammalian host cell may be selected from any mammalian species, such as human cell types, including without limitation, cells such as Vero cells, A549 and HKB cells. Other mammalian species cells are also useful, for example, primate cells, rodent cells or other cells commonly used in biological laboratories. The selection of the mammalian species providing the cells is not a limitation of this invention; nor is the type of mammalian cell, i.e., fibroblast, hepatocyte, tumor cell, etc.

B. Transforming DNA Molecule

Suitably, the target cells are transformed with a DNA molecule carrying, at a minimum, DNA sequences encoding adenovirus E1a and E1b under the control of a PGK promoter. This molecule lacks adenoviral sequences 5' of the E1 region, preferably excluding the native E1a promoter and contains minimal sequences 3' to the E1 region (i.e., optionally contains partial pIX sequences).

The DNA sequences encoding the adenovirus E1a and E1b genes useful in this invention may be selected from among any known adenovirus type, including the presently identified 41 human types. Similarly, adenoviruses known to infect other animals may supply the gene sequences. The selection of the adenovirus type for each E1a and E1b gene sequence does not limit this invention. The sequences for a number of adenovirus serotypes, including that of serotype Ad5, are available from Genbank. A variety of adenovirus strains are available from the ATCC, or are available by request from a variety of commercial and institutional sources. In the following exemplary embodiment the E1a and E1b gene sequences are those from adenovirus serotype 5 (Ad5).

By "adenoviral DNA which expresses the E1a gene product", it is meant any adenovirus gene encoding E1a or any functional E1a portion. Similarly included are any alleles or other modifications of the E1a gene or functional portion. Such modifications may be deliberately introduced by resort to conventional genetic engineering or mutagenic techniques to enhance the E1a expression or function in some manner, as well as naturally occurring allelic variants thereof.

By "adenoviral DNA which expresses the E1b gene product", it is meant any adenovirus gene encoding E1b or any functional E1b portion. Similarly included are any alleles or other modifications of the E1b gene or functional portion. Such modifications may be deliberately introduced by resort to conventional genetic engineering or mutagenic techniques to enhance the E1b expression or function in some manner, as well as naturally occurring allelic variants thereof The nucleic acid molecule carrying the Ad E1a and Ad E1b may be in any form which transfers these components to the host cell. Most suitably, these sequences are contained within a vector. A "vector" includes, without limitation, any genetic element, such as a plasmid, phage, transposon, cosmid, chromosome, virus, virion, etc. In one particularly suitable embodiment, the nucleic acid molecule is a plasmid carrying Ad E1a, Ad E1b, partial pIX sequences, and the PGK promoter.

The nucleic acid molecule may contain other non-viral sequences, such as those encoding certain selectable reporters or marker genes, e.g., sequences encoding hygromycin or purimycin, or the neomycin resistance gene for G418 selection, among others. The molecule may further contain other components.

Conventional techniques may be utilized for construction of the nucleic acid molecules of the invention. See, generally, Sambrook et al, Molecular Cloning: A Laboratory Manual, Cold Spring Harbor Laboratories, Cold Spring Harbor, N.Y.

Once the desired nucleic acid molecule is engineered, it may be transferred to the target cell by any suitable method. Such methods include, for example, transfection, electroporation, liposome delivery, membrane fusion techniques, high velocity DNA-coated pellets, viral infection and protoplast fusion. Thereafter, cells are cultured according to standard methods and, optionally, seeded in media containing an antibiotic to select for cells containing the cells expressing the resistance gene. After a period of selection, the resistant colonies are isolated, expanded, and screened for E1 expression. See, Sambrook et al, cited above.

II. Use of E1-Complementing Cells in Production E1-Deleted Adenovirus

The E1-complementing cells of the invention are useful for a variety of purposes. Most suitably, the cells (e.g., GH329) are used in packaging recombinant virus (i.e., viral particles) from E1-defective vectors and in high yield production of E1-defective adenoviruses in the absence of detectable RCA.

The cells of the invention which express Ad5 E1a and E1b are suitable for use in packaging recombinant virus from E1-defective vectors (e.g., plasmids) containing sequences of Ad5 and Ad2. Further, these cells are anticipated to be useful in producing recombinant virus from other Ad serotypes, which are known to those of skill in the art.

A. Packaging of E1-Defective Vectors

In a preferred embodiment, this method of the invention involves packaging of an E1-deleted vector which contains a transgene into an E1-deleted adenoviral particle useful for delivery of the transgene to a host cell. In a preferred embodiment, the E1-deleted vector contains all adenoviral genes necessary to produce and package an infectious adenoviral particle which replicates only in the presence of complementing E1 proteins, e.g., such as are supplied by cell line of the invention. The vector contains defects in both the E1a and E1b sequences, and most desirably, is deleted of all or most of the sequences encoding these proteins.

At a minimum, the E1-deleted vector to be packaged contains adenoviral 5' and 3' cis-elements necessary for replication and packaging, a transgene, and a pIX gene or a functional fragment thereof The vector further contains regulatory sequences which permit expression of the encoded transgene product in a host cell, which regulatory sequences are operably linked to the transgene. As used herein, "operably linked" sequences include both expression control sequences that are contiguous with the gene of interest and expression control sequences that act in trans or at a distance to control the gene of interest. Also included in the vector are regulatory sequences operably linked to other gene products, e.g., the pIX gene, carried by the vector.

1. Adenoviral Elements

The E1-defective vector to be packaged includes, at a minimum, adenovirus cis-acting 5' and 3' inverted terminal repeat (ITR) sequences of an adenovirus (which function as origins of replication) and the native 5' packaging/enhancer domain. These are 5' and 3' cis-elements necessary for packaging linear Ad genomes and further contain the enhancer elements for the E1 promoter.

The E1-deleted vector to be packaged into a viral particle is further engineered so that it expresses the pIX gene product. Most suitably, the pIX gene is intact, containing the native promoter and encoding the full length protein. However, were desired, the native pIX promoter may be substituted by another desired promoter. Alternatively, sequences encoding a functional fragment of pIX may be selected for use in the vector. In yet another alternative, the native sequences encoding pIX or a functional fragment thereof may be modified to enhance expression. For example, the native sequences may be modified, e.g., by site-directed mutagenesis or another suitable technique, to insert preference codons to enhance expression in a selected host cell. Optionally, the pIX may be supplied to the E1-complementing cell line on a separate molecule.

An exemplary vector containing only the minimal adenoviral sequences is termed the AdΔE1-E4 vector, and lacks all functional adenoviral genes including E1, E2, E3, E4, intermediate gene IXa and late genes L1, L2, L2, L4 and L5) with the exception of intermediate gene IX which is present. However, in a preferred embodiment, the E1-deleted vector contains, in addition to the minimal adenoviral sequences described above, functional adenoviral E2 and E4 regions. In another suitable embodiment, the adenoviral sequences in the E1-deleted vector include the 5' and 3' cis-elements, functional E2 and E4 regions, intermediate genes IX and IXa, and late genes L1 through L5. However, the E1-deleted vector may be readily engineered by one of skill in the art, taking into consideration the minimum sequences required, and is not limited to these exemplary embodiments.

The vector is constructed such that the transgene and the sequences encoding pIX are located downstream of the 5' ITRs and upstream of the 3' ITRs. The transgene is a nucleic acid sequence, heterologous to the adenovirus sequence, which encodes a polypeptide, protein, or other product, of interest. The transgene is operatively linked to regulatory components in a manner which permits transgene transcription.

2. Transgene

The composition of the transgene sequence will depend upon the use to which the resulting virus will be put. For example, one type of transgene sequence includes a reporter sequence, which upon expression produces a detectable signal. Such reporter sequences include without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art to which high affinity antibodies directed thereto exist or can be produced by conventional means, and fusion proteins comprising a membrane bound protein appropriately fused to an antigen tag domain from, among others, hemagglutinin or Myc.

However, desirably, the transgene is a non-marker sequence encoding a product which is useful in biology and medicine, such as proteins, peptides, anti-sense nucleic acids (e.g., RNAs), enzymes, or catalytic RNAs. The transgene may be used to correct or ameliorate gene deficiencies, which may include deficiencies in which normal genes are expressed at less than normal levels or deficiencies in which the functional gene product is not expressed. One desirable type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., total of the DNA encoding the subunits and the IRES is less than five kilobases. Other useful gene products include, molecules which induce an immune response, non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a gene. However, the selected transgene may encode any product desirable for delivery to a host or desirable for study. The selection of the transgene sequence is not a limitation of this invention.

3. Regulatory Sequences

In addition to the major elements identified above for the vector, (e.g, the adenovirus sequences and the transgene), the vector also includes conventional control elements necessary to drive expression of the transgene in a host cell containing with the transgene. Thus the vector contains a selected promoter which is linked to the transgene and located, with the transgene, between the viral sequences of the vector. Suitable promoters may be readily selected from among constitutive and inducible promoters. Selection of these and other common vector elements are conventional and many such sequences are available [see, e.g., Sambrook et al, and references cited therein].

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521–530 (1985)], the SV40 promoter, the dihydrofolate reductase promoter, the β-actin promoter, the phosphoglycerol kinase (PGK) promoter, and the EF1α promoter [Invitrogen]. Inducible promoters are regulated by exogenously supplied compounds, including, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346–3351 (1996)], the tetracycline-repressible system [Gossen et al, *Proc. Natl. Acad. Sci. USA*, 89:5547–5551 (1992)], the tetracycline-inducible system [Gossen et al, *Science*, 268:1766–1769 (1995), see also Harvey et al, *Curr. Opin. Chem. Biol.*, 2:512–518 (1998)], the RU486-inducible system [Wang et al, *Nat. Biotech.*, 15:239–243 (1997) and Wang et al, *Gene Ther.*, 4:432–441 (1997)] and the rapamycin-inducible system [Magari et al, *J. Clin. Invest.*, 100:2865–2872 (1997)].

4. Other Vector Elements

The vector carrying the Ad ITRs flanking the transgene and regulatory sequences (e.g., promoters, polyA sequences, etc.) may be in any form which transfers these components to the host cell. Preferably, the vector is in the form of a plasmid. Preferably to avoid homologous recombination, the plasmid does not contain any adenovirus sequences in the E1 region or the region 5' to the E1 region. It may contain non-viral sequences, such as those encoding certain selectable reporters or marker genes, e.g., sequences encoding hygromycin or purimycin, among others. Other components of the plasmid may include an origin of replication and an amplicon, such as the amplicon system, employing the Epstein Barr virus nuclear antigen, for example, the vector components in pCEP4 (Invitrogen). See, also, J. Horvath et al, *Virology*, 184:141–148 (1991). This amplicon system or similar amplicon components permit high copy episomal replication in the cells.

Other heterologous nucleic acid sequences optionally present in this vector include sequences providing signals required for efficient polyadenylation of the RNA transcript, and introns with functional splice donor and acceptor sites. A common poly-A sequence which is employed in the vectors useful in this invention is that derived from the papovavirus SV-40. The poly-A sequence generally is inserted following the transgene sequences and before the 3' AAV ITR sequence. A vector useful in the present invention may also contain an intron, desirably located between the promoter/enhancer sequence and the transgene. One possible intron sequence is also derived from SV-40, and is referred to as the SV-40 T intron sequence. Selection of these and other common vector elements are conventional and many such sequences are available [see, e.g., Sambrook et al, and references cited therein at, for example, pages 3.18–3.26 and 16.17–16.27].

5. Co-Transfection of adenoviral Sequences

Preferably, the E1-deleted vector contains all functional adenoviral sequences required for packaging and replication in the presence of the E1-complementing cell line of the invention. In addition to the E1a and E1b functions supplied by the trans-complementing cell line, functional adenoviral E2a and E4 ORF 6 region are required. However, where the required functions are lacking from the E1-deleted vector (i.e., the E1-deleted vector further contains functional deletions in E2a and/or E4 ORF6), these functions may be supplied by other sources. In one embodiment, these functions may be supplied by co-transfection of the E1-complementing cell line with one or more nucleic acid molecules capable of directing expression of the required adenoviral function. Alternatively, a modified GH329 cell line of the invention which has been transformed to supply the required adenoviral functions may be utilized.

For example, a vector deleted of E1 and having a defective E2 region may be complemented in GH329 cells of the invention by transfecting the cells with a nucleic acid molecule (e.g., a plasmid) expressing required E2 functions (e.g., E2a). As another example, a vector lacking E1 through E4 functions may be complemented in GH329 cells by transfecting the cells with a nucleic acid molecule expressing functional E2, E3 and E4 (e.g., E4 ORF6). Where a nucleic acid molecule is co-transfected into the cells of the invention, such a nucleic acid molecule contains no adenoviral E1 sequences; nor does it contain any sequences 5' to the E1 region. Construction of these nucleic acid molecules is within the skill of those in the art.

Suitably, a selected recombinant vector, as described above, is introduced into E1-complementing cells from a cell line of the invention using conventional techniques, such as the transfection techniques known in the art [see, K. Kozarsky et al, *Som. Cell and Molec. Genet.*, 19(5):449–458 (1993)]. Thereafter, recombinant E1-deleted adenoviruses are isolated and purified following transfection. Purification methods are well known to those of skill in the art and may be readily selected. For example, the viruses may be subjected to plaque purification and the lysates subjected to cesium chloride centrifugation to obtain purified virus.

B. Amplification of E1-Deleted Adenoviruses

The E1-trans-complementing cell line of the invention (or a derivative thereof) may be used to amplify an E1-defective adenovirus. Suitably, the E1-defective adenovirus will have been isolated and purified from cellular debris and other viral materials prior to use in this method. This is particularly desirable where the E1-defective adenovirus to be amplified is produced by methods other than those of the present invention. Suitable purification methods, e.g., plaque purification, are well known to those of skill in the art.

A culture, or preferably, a suspension of cells from an E1-trans-complementing cell line of the invention, e.g., GH329, are infected with the E1-defective adenovirus using conventional methods. A suitable multiplicity of infection (MOI) may be readily selected. However, an MOI in the range of about 0.1 to about 100, about 0.5 to about 20, and/or about 1 to about 5, is desirable. The cells are then cultured under conditions which permits cell growth and replication of the E1-defective adenovirus in the presence of the E1 expressed by the cell line of the invention. Suitably, the viruses are subjected to continuous passages for up to 5, 10, or 20 passages. However, where desired, the viruses may be subjected to fewer, or more passages.

The cells are subjected to two to three rounds of freeze-thawing, the resulting lysate is then subjected to centrifugation for collection, and the supernatant is collected. Conventional purification techniques such as chloride gradient centrifugation or column chromatography are used to concentrate the rAd-ΔE1 from the cellular proteins in the lysate. Advantageously, however, the method of the invention through use of the cell lines of the invention avoid the problems of contaminating RCA which plague conventional production techniques.

III. E1-Deleted Ad produced by method of invention

The E1-deleted adenoviruses produced according to the present invention are suitable for a variety of uses and are particularly suitable for in vivo uses, as the present invention permits these adenoviruses to be produced in serum-free media, and in the absence of detectable RCA. Thus, the E1-deleted adenoviruses produced according to the invention are substantially free of contamination with RCA.

In one embodiment, E1-deleted viruses have been deemed suitable for applications in which transient transgene expression is therapeutic (e.g., p53 gene transfer in cancer and VEGF gene transfer in heart diseases). However, the E1-deleted adenoviruses are not limited to use where transient transgene expression is desired. The E1-deleted adenoviruses are useful for a variety of situations in which delivery and expression of a selected transgene is desired.

Suitable doses of E1-deleted adenoviruses may be readily determined by one of skill in the art, depending upon the condition being treated, the health, age and weight of the veterinary or human patient, and other related factors. However, generally, a suitable dose may be in the range of $10^{10}$ to $10^{18}$, and preferably about $10^{14}$ to $10^{16}$ viral particles per dose, for an adult human having weight of about 80 kg. This dose may be suspended in about 0.01 mL to about 1 mL of a physiologically compatible carrier and delivered by any suitable means. The dose may be repeated, as needed or desired, daily, weekly, monthly, or at other selected intervals.

The following examples are provided to illustrate the production of the exemplary cell lines of the invention and their use in producing E1-deleted adenovirus which are free of detectable RCA over 20 passages. These examples do not limit the scope of the invention. One skilled in the art will appreciate that although specific reagents and conditions are outlined in the following examples, modifications can be made which are meant to be encompassed by the spirit and scope of the invention.

EXAMPLE 1

Production of E1-complementing Cell Lines

As described in this example, Vero, A549 and HeLa cells were stably transfected with plasmid constructs carrying a 3.4 kb DNA fragment of Ad 5 genome spanning 511 to 3924 bp (E1a and E1b open reading frames and part of the pIX gene). FIG. 1 is provides a schematic representation of the relevant constructs. In these constructs, the E1a native promoter was replaced with either sequences from the cytomegalovirus early gene (CMV) or human phosphoglycerate kinase gene (PGK). There is no overlap with the 5' region of the E1-deleted vector (0–360 bp) described below and reduced overlap at the 3' region (vector begins at 3312 bp while the adenovirus sequence in 293 extends to 4300 bp).

A. Construction of PGKE1 plasmids

Ad5 E1 region (m.u. 1.42–10.9) was cloned into pBluescript SK(–) vector. The 3.4 kb E1 fragment was further subcloned into a plasmid which allowed expression from promoters derived from the phosphoglycerate kinase gene [PGK] [Adra et al., Gene, 60:65–74 (1987)] or the immediate early gene of cytomegalovirus [CMV] [Thomsen et al., *Proc. Natl. Acad. Sci. USA*, 81:659–663 (1984)]. Both contained the neomycin resistance gene for G418 selection.

B. Transfections and selection of G418-resistant clone

HeLa, A549 and Vero cells were obtained from ATCC and maintained as monolayers in Dulbecco modified Eagle's minimal essential medium (DMEM) supplemented with 10% fetal bovine serum. Plasmids were transfected by calcium phosphate precipitation onto the cells seeded in 100 mm plates, using 10 μg of plasmid DNA for each plate. Twenty-four hours post-transfection, cells were trypsinized and seeded in G418-containing media at various dilutions ranging from 1:5 to 1:40. After 2 weeks of selection, G418-resistant colonies were isolated, expanded and screened for E1 expression.

Only one stable clone formed from A549 transfectants, while over 70 clones from HeLa and 50 clones from Vero cell transfectants were isolated (data not shown).

C. Screening procedure for new E1 lines

Stable G418-resistant clones were first screened with a blue comet formation assay in which $1\times10^6$ cells in 6 well plates were infected with 200 LacZ Forming Units (LFU) of H5.CBLacZ [an E1-deleted adenovirus expression LacZ from a β-actin promoter] [Gao et al., *J. Virol.*, 70:8934–8943 (1996)]. Six days post-infection cells were histochemically stained with 5-Bromo-4-chloro-3-indolyl-β-D-galactopyranoside (X-gal) and comets of blue cells in each well were scored. Subsequently, the strongly positive clones were seeded into 4 well glass chamber slides for 24 hours. Expression level of E1a and E1b proteins in the cells was assessed by immunofluorescent staining, using mouse monoclonal antibodies (Oncogene Science).

G418 resistant clones were expanded and initially screened for their ability to support propagation of an E1-deleted adenovirus vector harboring the LacZ transgene; the only clones capable of sustaining E1-deleted adenovirus replication were HeLa derived.

EXAMPLE 2

Characterization of new E1 complementing cell lines.

A. Genetic constitution

Total genomic DNAs were isolated from each E1 complementing clone, digested with appropriate restriction endonucleases to release an internal E1-containing plasmid fragment, and evaluated by DNA hybridization after electrophoresis. More particularly, DNAs were fractionated on 1% agarose gels, transferred to nylon filters and hybridized with a 1.1 kb E1 Hind III/Sma I fragment.

All cell lines tested have at least one copy of the E1 gene integrated into HeLa genome. One PGK-E1 clone (GH364) and one CMV-E1 cell line (GH414) harbor 5–10 copies of the E1 gene.

B. Production of E1 proteins

Cell pellets of each clone were harvested from 60 mm plates and resuspended in 200 μl of lysis buffer (20 mM Tris-Cl, pH 8.0, 140 mM NaCl, 1% NP-40 v/v, 1 mM PMSF, 1 μg/ml each leupeptin, antipain, chymostatin, soybean trypsin inhibitor). Lysates were incubated on ice for one hour and spun in a microcentrifuge at 14,000 rpm for 30 minutes at 4° C. Supernatants were collected and total protein concentrations determined by Lowry's method. Samples (50 μg) were fractionated on 10% SDS-PAGE gels and electrotransferred to nitrocellulose membranes. E1a and E1b proteins were detected using the enhanced chemiluminescence (ECL) system (Amersham Life Science, Arlington Heights, Ill.) with a mouse polyclonal antibody (PharmMingen, San Diego, Calif.) and rat monoclonal antibodies (Oncogene Science) respectively. Total cellular proteins from 293 cells were used as controls.

Western blot analysis revealed variable E1 protein expression profiles among different clones, in terms of total expression and the ratios of E1a and E1b proteins. The anti-Ad5 antibody identified the E1a protein as a doublet at approximately 35–46 kDa.

C. Growth kinetics of an E1-deleted recombinant virus H5.CBLacZ on the novel E1 complementing cell lines HeLa, 293 and the cells of new E1 cell lines were infected with H5.CBLacZ at multiplicity of infection (MOI) equal to 0.5. Infected cells were harvested at 24, 48, 72, 96 and 120 hours post-infection. Cells were lysed in the infection medium by 3 rounds of freeze/thaw and the titer of virus was determined by serial dilution infections on 293 cells followed by histochemical staining with X-gal. Cells were histochemically stained with X-gal after 20 hours, and blue cells were counted. Titers are expressed as LacZ forming units (LFU/ml) where one LFU is defined as the quantity of virus sufficient to cause visually detectable LacZ expression in one cell at 24 hour post-infection.

Figure 2A:
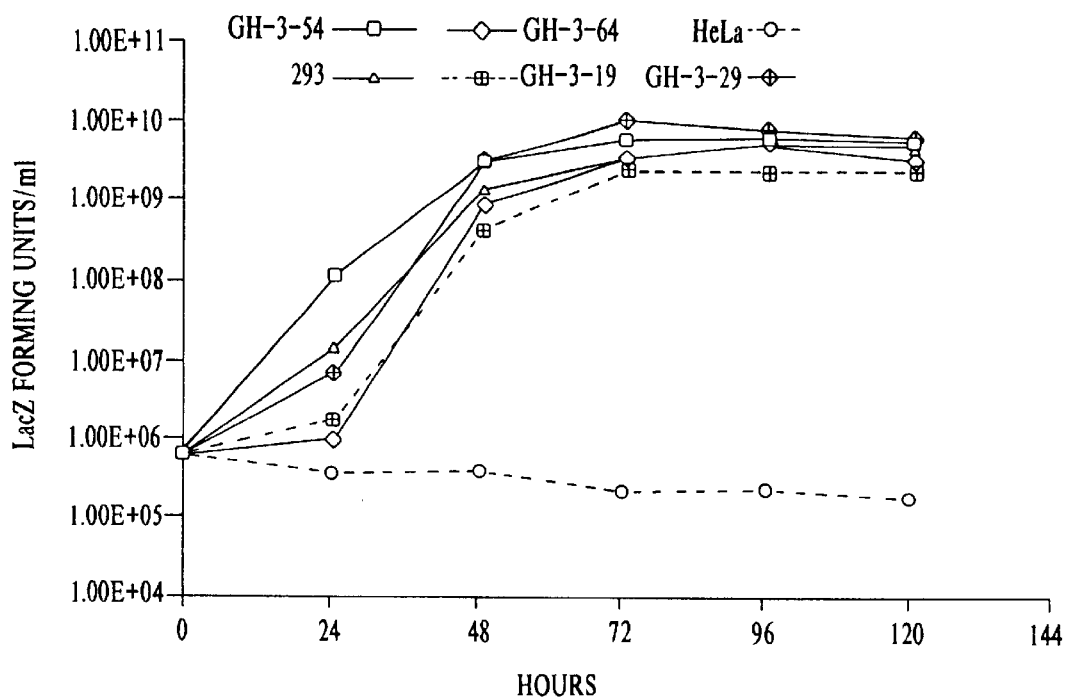
FIG. 2A is a graph of the growth kinetics of an E1-deleted recombinant adenovirus, H5.CBLacZ, in 293 and new E1 cell lines. See Example 2C for details of the study. The yield of H5.CBLacZ virus in each cell line is shown on they axis in a log scale. The time points are shown on the x axis.

The yield of H5.CBLacZ virus in each cell line is shown on FIG. 2A, where the y axis is a log scale and the time points are shown on the x axis. Two cell lines, GH329 and GH354, were equivalent if not better than 293 cells in terms of production (FIG. 2A) of E1-deleted virus.

D. Relative plaguing efficiencies (RPEs) for H5.CBLacZ virus on new E1 cell lines The new E1 cell lines were compared with 293 cells in their abilities to support plaque formation of H5.CBLacZ virus. Cells were infected with H5.CBLacZ with a range of serial dilutions and overlaid with top agar after 20 hours. Plaques were detected by staining with neutral red on day 10 post infection. RPEs were computed as the percentage of the titer of H5.CBLacZ virus as compared to that on 293 cells. Cells were infected with H5.CBLacZ over a range of serial dilutions and overlaid with top agar after 20 h.

Figure 2B:
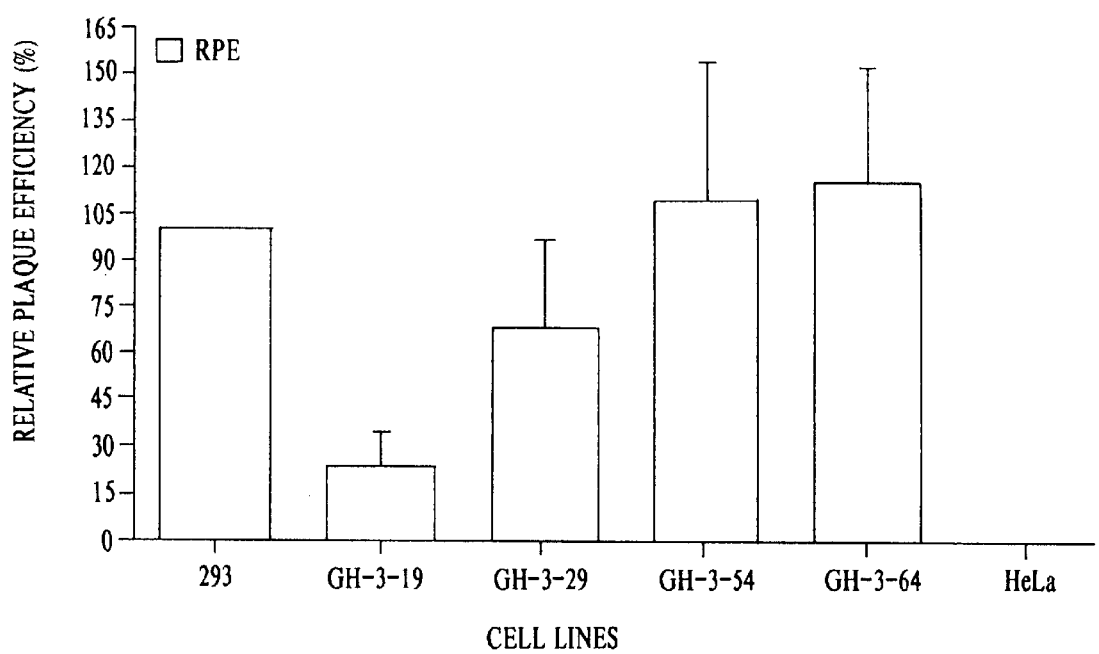
FIG. 2B is a bar chart showing the relative plaquing efficiency (RPE) for H5.CBLacZ virus on new E1 cell lines which were compared with 293 cells. See Example 2D for details of the study. RPEs were computed as the percentage of the titer of H5.CBLacZ virus. Solid bars, the mean RPE of each cell line from three different experiments; error bars represent standard deviations.

Plaques were detected by staining with neutral red on day 10 post infection. RPEs were computed as the percentage of the titer of H5.CBLacZ virus. Solid bars, the mean RPE of each cell line from three different experiments; error bars, standard deviations. Two cell lines, GH329 and GH354, were equivalent if not better than 293 cells in terms of plaquing efficacy (FIG. 2B) of E1-deleted virus.

EXAMPLE 3

Detection of RCAs in the E1-deleted recombinant virus preps after multiple passages in either 293 or GH329 cells The propensity to generate RCA was studied by serially passaging an E1-deleted LacZ virus (initially isolated on GH329) and both GH329 and 293 cells. A portion of each lysate was used to infect a non-E1 expressing cell line (A549) to assess for RCA, which presented itself as cytopathology on serial passage and was confirmed by DNA hybridization analysis, as follows. However, since crude Hirt DNAs were used for the Southern blot analysis, it would be difficult to use the assay to quantify the amount of RCAs in each sample.

H5.CBLacZ virus was plaque-purified twice on GH329 cells following the standard protocol (Gao et al., *J. Virol.*, 70:8934–8943 1996)]. The blue plaques identified by X-gal histochemical staining were selected, expanded to a large prep in GH329 cells and purified by CsCl gradient centrifugation. The purified H5.CBLacZ virus was designated as passage 0 (P0) and used for continuous passages on 293 and GH329 cells simultaneously for up to 20 passages. Large-preparation viruses grown up in each cell line were CsCl gradient-purified from passages 5, 10, 15 and 20. A549 cells were obtained from ATCC and cultured in F-12K medium supplemented with 10% FBS. For the RCA assay, cells were seeded at a density of $1\times10^7$ cells per an 150 mm plate 24 hours prior to the virus infection. A total of $1\times10^8$ PFU each of testing viruses were diluted in 80 ml of F-12K medium with 2% fetal bovine serum (FBS) and 1% penicillin/streptomycin (P/S) and added to four 150 mm plates of A549 cells after removal of the growth medium from each plate. At 24 hours post infection, 1.6 mls of FBS were added into each plate. As a positive control, 1 PFU of Ad5 wild type virus was spiked into each of $1\times10^8$ PFU testing articles for the infection procedure described above. Negative control plates were also analyzed in parallel. Infected cells from each plate were harvested at 14 days later and lysed in infection medium by three rounds of freezing-thawing. Twenty percent of total cell lysate from each plate were used to infect one plate of A549 cells following the protocol described above. Seven days post infection, the plates were examined under a light microscope for cytopathic effects.

The RCA assay used in this study can detect 1 PFU of RCA in 10$^8$ PFUs of recombinant viruses. The infected cells from each plate were harvested with the medium and spun down for collection of the cell pellet. Each cell pellet was resuspended in 0.5 ml of 10 mM Tris-Cl, pH 8.0 and lysed by three cycles of freezing-thawing. After centrifugation in a Sorvall-26 at 3,200 rpm for 15 min, the supernatant of each sample was collected. One-third of each supernatant was mixed with an equal volume of 2× pronase solution (2 mg/ml pronase, 100 mM Tris-Cl, pH 7.6, 2 mM EDTA, 1% SDS, incubate the solution at 37 C. for 45 min), incubated at 37° C. for 4 hours, extracted with phenol-chloroform and ethanol precipitated. The crude viral DNA samples were resuspended in equal volume of TE buffer and subjected to Nsi I endonuclease digestion and Southern blot analysis. Blots were hybridized with a 420 bp E1-Xba I/Cla I DNA probe.

The results showed that significant RCA emerged between passage 5 and 10 on 293 cells whereas no RCA was detected after 20 passages on GH329. The sensitivity of the RCA assay was confirmed by spiking a zero passage GH329 cells in the presence of vector with 1 pfu of wild type Ad.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. An E1-complementing cell line comprising an aneuploid cell line stably transformed with a nucleic acid molecule comprising nucleic acid sequences encoding adenovirus E1a and adenovirus E1b under the control of a phosphoglycerate kinase (PGK) promoter, and wherein the nucleic acid molecule and cell line lacks adenovirus sequences 5' to the sequences encoding adenovirus E1a, wherein the aneuploid cell line is a HeLa cell line.

2. The E1-complementing cell line according to claim 1, wherein the nucleic acid sequences farther comprise nucleic acid sequences of the pIX gene region.

3. The E1-complementing cell line according to claim 1, wherein the nucleic acid molecule is a plasmid vector.

4. The E1-complementing cell line according to claim 1, wherein the nucleic acid molecule comprises multiple copies of the sequences encoding adenovirus E1a and adenovirus E1b.

5. The E1-complementing cell line according to claim 1, wherein the E1-complementing cell line comprises multiple copies of the nucleic acid molecule.

6. The E1-complementing cell line according to claim 1, wherein the sequences encoding adenovirus E1a and the sequences encoding E1b are independently selected from adenovirus type 5.

7. An adenovirus E1-complementing cell line having the characteristics of GH364, ATCC PTA-3405.

8. An adenovirus E1-complementing cell line designated GH329, deposited with the ATCC under accession number PTA-803.

9. An adenovirus E1-complementing cell line having the characteristics of GH354, ATCC PTA-3405.

10. A method of generating an E1-complementing cell, comprising the steps of transforming a cell selected from the group consisting of GH329, ATCC PTA-803; GH364, ATCC PTA-3405; and GH354, ATCC PTA-3404 with a nucleic acid molecule comprising a desired nucleic acid sequence.

11. A method of generating an E1-complementing cell, comprising the steps of transforming a HeLa cell with a nucleic acid molecule comprising DNA sequences encoding adenovirus E1a and E1b under the control of a PGK promoter, wherein said nucleic acid molecule lacks the native E1a promoter and adenovirus sequences 5' of the E1 open reading frame.

12. A method for packaging of E1-defective adenoviral particles in the absence of replication competent adenovirus, said method comprising the steps of:

(a) providing cells from an E1-complementing cell line comprising an aneuploid HeLa cell line stably transformed with a nucleic acid molecule comprising nucleic acid sequences encoding adenovirus E1a and adenovirus E1b under the control of a phosphoglycerate kinase (PGK) promoter, wherein the nucleic acid molecule and cell line lacks adenovirus sequences 5' to the sequences encoding adenovirus E1a;

(b) transfecting said cells with a recombinant vector comprising, from 5' to 3', adenovirus 5' inverted terminal repeat sequences (ITRs), nucleic acid sequences encoding adenovirus pIX under the control of sequences which direct expression of adenovirus pIX in said cells, and a defect in the adenovirus E1 region, and adenovirus 3' ITRs; and (c) culturing said transfected cells under conditions which permit packaging of the E1-defective vector into a recombinant E1-defective adenoviral particle.

13. The method according to claim 12, further comprising the step of transfecting said cells with a second recombinant vector comprising adenovirus sequences encoding at least one adenoviral gene and a defect in the adenovirus E1 region.

14. The method according to claim 13, wherein said second recombinant vector encodes adenovirus E2a.

15. The method according to claim 13, wherein said second recombinant vector encodes adenovirus E4 or a functional fragment thereof.

16. The method according to claim 15, wherein the functional fragment is E4 ORF6.

17. The method according to claim 12, wherein said recombinant vector further comprises a selected transgene.

18. The method according to claim 17, wherein said transgene is located between the 5' and 3' ITRs.

19. The method according to claim 12, wherein the E1-complementing cell line is selected from the group consisting of GH329, ATCC PTA-803; GH364, ATCC PTA-3405; and GH354, ATCC PTA-3404.

20. A method of amplifying E1-defective adenoviral particles in the absence of replication competent adenovirus, the method comprising the steps of:

(a) infecting an E1-complementing cell line with E1-defective adenoviruses, wherein said cell line comprises an aneuploid HeLa cell line stably transformed with a nucleic acid molecule comprising nucleic acid sequences encoding adenovirus E1a and adenovirus E1b under the control of a phosphoglycerate kinase (PGK) promoter, and wherein the nucleic acid molecule and cell line lack adenovirus sequences 5' to the sequences encoding adenovirus E1a;

(b) passaging the E1-defective adenoviral particles on the E1-complementing cell line for 2 to 20 passages, and (c) collecting the E1-defective adenoviral particles.

21. The method according to claim 20, wherein the E1-defective adenoviruses of (a) are prepared by the steps comprising:

(i) providing cells from an E1-complementing cell line comprising an aneuploid HeLa cell line stably transformed with a nucleic acid molecule comprising nucleic acid sequences encoding adenovirus E1a and adenovirus E1b under the control of a phosphoglycerate kinase (PGK) promoter, wherein the nucleic acid sequences further comprise a deletion of adenovirus sequences 5' to the sequences encoding adenovirus E1a;

(ii) transfecting said cells with a recombinant vector comprising adenovirus 5' and 3' inverted terminal repeat sequences (ITRs), nucleic acid sequences encoding adenovirus pIX under the control of sequences which direct expression of adenovirus pIX in said cells, and a defect in the adenovirus E1 region;

(iii) culturing said transfected cells under conditions which permit packaging of the E1-defective vector into a recombinant E1-defective adenoviral particle; and (iv) purifying the recombinant E1-defective adenoviral particle from substantially all cellular debris.

22. The method according to claim 20, wherein the E1-complementing cell line is selected from the group consisting of GH329, ATCC PTA-803; GH364, ATCC PTA-3405; and GH354, ATCC PTA-3404.

* * * * *